(12) United States Patent
Busacca

(10) Patent No.: US 6,316,620 B1
(45) Date of Patent: Nov. 13, 2001

(54) ELECTRONICALLY TUNED LIGANDS

(75) Inventor: Carl A. Busacca, Poughkeepsie, NY (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 09/655,115

(22) Filed: Sep. 5, 2000

Related U.S. Application Data

(60) Provisional application No. 60/152,909, filed on Sep. 8, 1999.

(51) Int. Cl.$^7$ .................... C07F 9/02; C07F 9/28
(52) U.S. Cl. ............... 544/243; 544/244; 548/310.7; 548/335.1
(58) Field of Search .................. 544/243, 244; 548/310.7, 335.1

(56) References Cited

PUBLICATIONS

Jacobsen, E. N. et al, Electronic Tuning of Asymmetric Catalysts, J. Am. Chem Soc., 1991, 6703–6705, vol. 113, No. 17, American Chemical Society, Washington, DC, US.

Loiseleur, O. et al, Enantioselective Heck Reactions Catalyzed by Chiral Phosphinooxazoline–Palladium Complexes, Synthesis, 1997, 1338—1345, No. 11, Georg Thieme Verlag. Stuttgart, DE.

Allen, J.V. et al, Preparation of Novel Sulfur and Phosphorus Containing Oxazolines as Ligands for Asymmetric Catalysis, Tetrahedron, 1994, 799—808, vol. 50, No. 3, Elsevier Science Publishers, Amsterdam, NL.

Peer, M. et al, Preparation of Chiral Phosphorus, Sulfur and Selenium Containing 2–Aryloxazolines, Tetrahedron, 1996, 7547—7583, vol. 52, No. 21, Elsevier Science Publishers, Amsterdam, NL.

Loiseleur, O. et al, Enantioselective Heck reactions using chiral P, N–Ligands, Journal of Organometallic Chemistry, 1999, 16—22, vol. 576, No. 1–2, Elsevier–Sequoia S.A. Lausanne.

*Primary Examiner*—Mukund J. Shah
*Assistant Examiner*—Huang Liu
(74) *Attorney, Agent, or Firm*—R. P. Raymond; MτE. M. Devlin

(57) ABSTRACT

A new class of chiral bidentate ligands to transition metals is disclosed which compounds have the following structure:

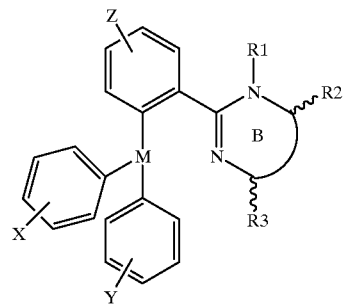

wherein the substituents are as defined herein.

2 Claims, No Drawings

ELECTRONICALLY TUNED LIGANDS

This application claims the benefit of U.S. Provisional Application No. 60/152,909, filed Sep. 8, 1999.

BACKGROUND OF THE INVENTION

Asymmetric synthesis is becoming more and more important in the pharmaceutical industry. There is growing regulatory pressure to approve only those enantiomers of drugs that have the desired biological activity. For safety reasons and to demonstrate efficacy, regulatory agencies are taking the position that only those enantiomers with pharmaceutical action should be administered, apart from the enantiomers with little or no action or even adverse or toxic effect. The total market for enantiomerically pure pharmaceuticals is projected to be ninety billion U.S. dollars by 2000. To prepare such large quantities of drug only via resolution will often be cost prohibitive. Chiral catalysis will no doubt complement traditional methods such as resolution or chiral separation. Many asymmetric syntheses involve use of catalysts, and typically employ chiral ligands and late transition metals. Bidentate ligands play a central role in catalyst design for asymmetric synthesis. Ligands that have been used successfully in asymmetric synthesis include the BINAP family of catalysts for asymmetric reductions and isomerizations (For example, see *Asymmetric Catalysis in Organic Synthesis*, Noyori, R., Ed.; John Wiley and Sons: New York, 1994, p.16–121).

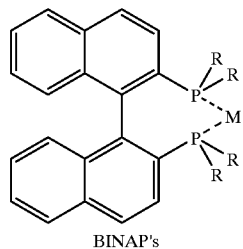

BINAP's
M is Pd, Rh, Ru or Ir;
R is phenyl, substituted phenyl or alkyl

Bisoxazolines for asymmetric cyclopropanation and cycloadditions have been reported (For a review, see Ghosh, A. K.; Mathivanan, P.; and Cappiello, J. *Tetrahedron: Asymmetry* 1998,9, 1–45).

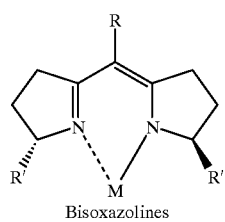

Bisoxazolines
M is Cu, Mg, Fe, Ni, Co, Ru or Pd
R is CN or alkyl;
R' is alkyl, aryl, substituted alkyl, benzyl, Pyridyloxazolines for asymmetric hydrosilations have also been described (Brunner, H.; Obermann, U. *Chem. Ber.* 1989, 122, 499).

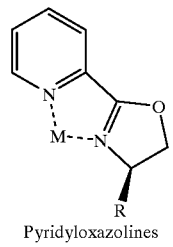

Pyridyloxazolines
M is Rh;
R is i-Pr, t-Bu, aryl, benzyl, or substituted alkyl.

Even more recently, electronically "mixed" bidentate ligands with two different ligating heteroatons (N—O, P—N, P—O) have emerged. Such ligands have been shown empirically to outperform P—P bidentate ligands in a number of synthetically important transformations. Such "mixed" ligands are the phosphino-oxazolines described by Pfaltz et al. (Synthesis, 1997, 1338), Helmchen et al. (*Angew. Chem. Int. Ed. Eng.*, 1997, 36 (19)2108), and Williams et al., (*Tetrahedron*, 1994, 50, 9).

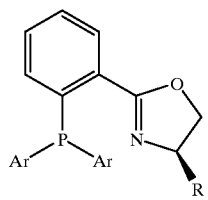

Phosphino-oxazolines
R is aryl, i-Pr, t-Bu, or benzyl.

The Heck reaction is one of the most versatile catalytic methods for C—C bond formation. In this reaction, an aryl or alkenyl halide or triflate is coupled with an alkene, as shown in the following scheme:

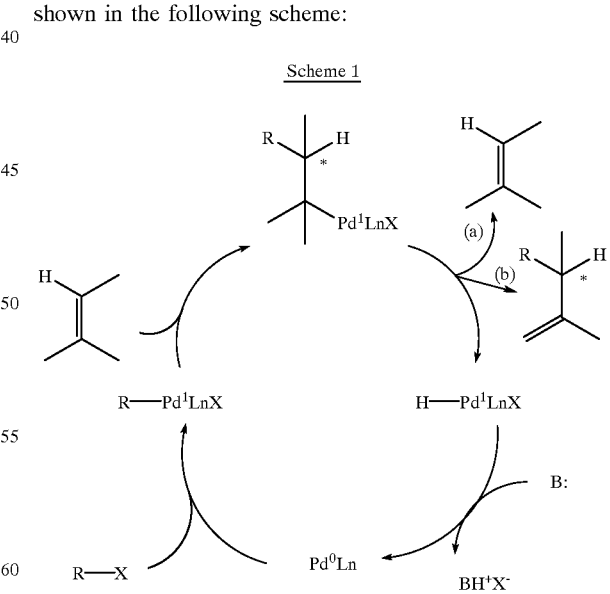

Scheme 1

The catalytic cycle starts with an oxidative addition of organic halide or triflate to a Pd (0) complex, followed by insertion of an alkene. The resulting Pd (II) alkyl complex then undergoes β-hydride elimination. Several isomeric products can be formed, depending upon the structure of the substrate. In path (a), the C—C double bond is restored in the original position and a stereogenic center is not created. However, if β-hydride elimination takes path (b), the stereogenic C atom introduced in the insertion step is retained. For path (b), the use of chiral palladium complexes makes it possible to perform such reactions in an enantioselective manner. Pfaltz et al. showed that chiral phosphino-oxazolines are very efficient ligands for enantioselective Heck reactions (Synthesis 1997, 1338). For example, asymmetric Heck arylation, using Pd/phosphino-oxazolines, produces substituted dihydrofuran in 90% yield and 92% ee, as shown below:

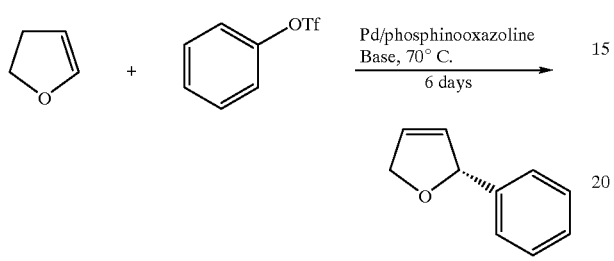

The phosphino-oxazolines described and taught by Pfaltz et al., Helnchen et al. and Williams et al. are superior to BINAP catalysts in the Heck reaction in that: (a) such ligands are insensitive to the nature of the added base; (b) have more ability to suppress side products; and (c) have very high enantioselectivity. However, such phosphino-oxazolines have a major deficiency. The above Heck arylation required six (6) days, an extremely long reaction time. It appears that the R substituent of the phosphino-oxazolines is not in conjugation with the ligating atoms, and therefore functions solely in a steric role. From the long reaction time or the low turnover of these catalysts, it is clear that the donicity of the bidentate ligand is not optimized.

THE INVENTION

A new class of chiral bidentate ligands to transition metals has been discovered. Such ligands can be electronically tuned at will for optimum performance. (For an example of electronic tuning in asymmetric catalysis using a different ligand class see: E. N. Jacobsen et al., *J Am. Chem. Soc.* 1991, 113, pp. 6703 –6704). Additionally, such ligands can be used to prepare chiral compounds of high optical purity. This new class of chiral ligands to transition metals can be easily tuned electronically by the replacement of a single substituent.

Here, and throughout this application unless otherwise specified, the term "alkyl" refers to a saturated aliphatic radical containing from one to ten carbon atoms. "Alkyl" refers to both branched and unbranched alkyl groups. Preferred alkyl groups are straight chain alkyl groups containing from one to eight carbon atoms and branched alkyl groups containing from three to eight carbon atoms. More preferred alkyl groups are straight chain alkyl groups containing from one to six carbon atoms and branched alkyl groups containing from three to six carbon atoms. "Alkyl", as used herein, includes unsubstituted alkyl radicals, those radicals that are partially or fully halogenated and those radicals substituted with one to four, preferably one or two, substituents selected from halo, amino, cyano, nitro, methoxy, ethoxy, hydroxy, keto, carboalkoxy, or amido. The term "cycloalkyl" refers to the cyclic analog of an alkyl group, as defined above. Preferred cycloalkyl groups are saturated cycloalkyl groups containing from three to eight carbon atoms, and more preferably three to six carbon atoms. "Alkyl" and "cycloalkyl", as used herein, include unsubstituted alkyl and cycloalkyl radicals, those radicals that are partially or filly halogenated and those radicals substituted with one to four, preferably one or two, substituents selected from halo, amino, cyano, nitro, methoxy, ethoxy, hydroxy, keto, carboalkoxy, or amido. It should be understood that any combination term using an "alk" or "alkyl" prefix refers to analogs according to the above definition of "alkyl". For example, terms such as "alkoxy", "alkylthio" refer to alkyl groups linked to a second group via an oxygen or sulfur atom.

The term "halo" or "halogen" refers to a halogen selected from fluoro, chloro, bromo, or iodo.

The new chiral bidentate ligands can be represented by Formula (1) below:

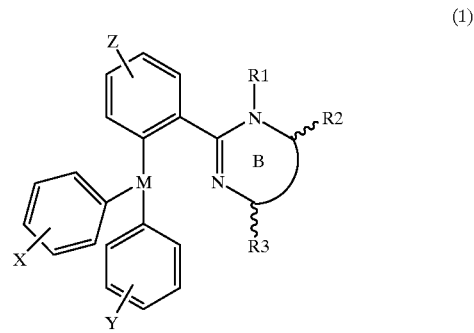

(1)

wherein

M is Phosphorus or Arsenic (P, As)

X, Y and Z can be independently selected from hydrogen, aryl (pendant or fused), halogen, alkyl, alkoxy, cyano, nitro, amino, alkylamino, dialkylamino, —CO$_2$H, —CO(C$_{1-6}$ alkoxy), —CO(C$_{1-6}$alkyl), —NCOH, —NCO(C$_{1-6}$alkyl), NSO$_2$(alkyl), —NSO$_2$(aryl), hydroxy, sulfonoxyalkyl, sulfonoxyaryl, or alkoxyalkyl.

R1 is selected from the group consisting of hydrogen, alkyl, branched alkyl, cycloalkyl, aryl selected from the group phenyl and naphthyl, which may optionally be substituted with one or more alkyl, halogen, alkoxy, acyl, phenoxy, cyano, nitro, hydroxy, amino, alkylamino, dialkylamino, carboalkoxy, amido, or sulfoxy group; heteroaryl selected from the group 2-pyridyl, 3-pyridyl, 4-pyridyl, 2-furyl, 3-furyl, 2-benzofuryl, 3-benzofuryl, 2-thiophenyl, 3-thiophenyl, 2-benzothiophenyl, 3-benzothiophenyl, 2-pyrrolyl, 3-pyrrolyl, 2-indolyl, 3-indolyl, benzimidazolyl, imidazolyl, quinolinyl, isoquinolinyl, oxazolyl, benzoxazolyl, thiazolyl, and pyrimidinolyl, which may be optionally substituted with one or more alkyl, halogen, alkoxy, acyl, phenoxy, cyano, nitro, hydroxy, amino, alkylamino, dialkylamino, carboalkoxy, amido, or sulfoxy group; C$_{2-6}$acyl, aroyl selected from the group benzoyl and napthoyl, optionally substituted one or more group as described above for aryl; heteroaroyl selected from the group 2-furoyl, 3-furoyl, 2-pyridoyl, 3-pyridoyl, 4-pyridoyl, 2-benzofuranoyl, 3-benzofuranoyl, 2-thiophenoyl, 3-thiophenoyl, 2-benzothiophenoyl, 3-benzothiophenoyl, 2-pyrroyl, 3-pyrroyl, 2-indoloyl, 3-indoloyl, benzimidazoyl, imidazoyl, quinolinoyl, isoquinolinoyl, oxazoyl, benzoxazoyl, thiazoyl, and pyrimidoyl, optionally substituted with one or more group as defined above for heteroaryl; SO$_2$R4 where R4 is chosen from the group alkyl, aryl and heteroaryl, which may be optionally substituted as described above.

R2 and R3 can be the same or different and can be selected from hydrogen, aryl or heteroaryl as defined above, substituted aryl or heteroaryl as defined above, (with substituents as defined above), alkyl, branched alkyl, cycloalkyl, benzyl, substituted benzyl, with substituents as defined for aryl, or R2 and R3 together may form a fused carbocyclic ring.

The amidine portion must be constrained to form a ring (ring B), and said ring must be either 5- or 6- membered. For example, B may be an imidazoline or tetrahydropyrimidine ring.

At least one, or both, of R2 and R3 must be attached to a chiral carbon, of either (R) or (S) absolute configuration.

The compounds of the present invention are particularly useful in Heck reactions. In such instances, preferred X,Y, and Z would be H, alkyl, aryl as described above, halogen, alkoxy, cyano, nitro, amino, alkylamino, and dialkylamnino. Preferred R1 would be H, alkyl, benzyl, aryl, substituted aryl as described above, heteroaryl and substituted heteroaryl as described above, $C_{2-6}$ acyl, and aroyl selected from the group of benzoyl, naphthoyl, and pyridoyl, optionally substituted with one or more groups as described above for aryl. Preferred R2,R3 would be H, alkyl, cycloalkyl, aryl and substituted aryl as described above, and heteroaryl and substituted heteroaryl as described above. Preferred B ring size might be five membered, that is, an imidazoline ring.

Solvent effects can be quite important in asymmetric synthesis. For the asymmetric Heck reaction in particular, the ligands of Formula (1) are most effective when used in a non-polar solvent. If a polar solvent is used, disappointing yields can be obtained that may vender use of the ligands of the present invention not commercially feasible.

The phosphino- and arsenoamidines of Formula (1) are electronically tunable. By varying the R1 substituent from electron withdrawing groups (e.g., acyl, benzoyl) to electron donating groups (e.g., alkyl, phenyl, benzyl), the basicity and donicity of the ligand can be easily modified and altered to suit the requirements of any given asymmetric synthesis.

To practice the instant invention, a complex is prepared between a ligand of Formula (1) and a transition metal, such as palladium. Other transition metals such as rhodium, ruthenium, iridium, nickel or platinum can be employed for catalyzed asymmetric hydrogenations. For catalyzed, enantioselective isomerization of allyl species, rhodium or cobalt would be employed. For catalyzed asymmetric cyclopropanations, rhodium, palladium or copper would be used. For catalyzed asymmetric hydroformylations of olefins, cobalt, rhodium, platinum or palladium would be used. Rhodium would also be used for catalyzed, asymmetric hydrosilylations of ketones. Rhodium or palladium would be used in catalyzed asymmetric hydrosilylation of olefms. However, this provides only a brief list of catalyzed, asymmetric reactions where the ligands of the instant invention could be successfully used.

The complex formed using the ligands of the present invention could be isolated or could be allowed to form in situ prior to addition of the substrate molecule. In general, the reaction would be allowed to proceed under the influence of the catalyst produced by the novel ligand until completion, the product then being isolated and optical purity measured.

The phosphino- and arsenoamidines of Formula (1) can be readily prepared from commercially available chiral amines or chiral amines which are themselves independently synthesized by methods known to those skilled in the art. Examples of such amines are the following:

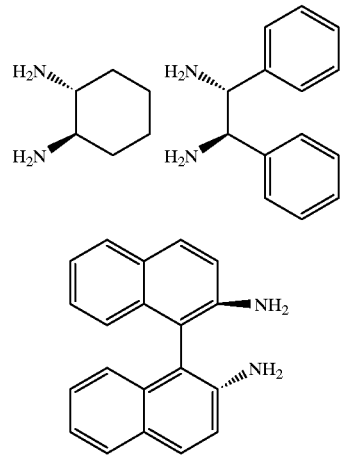

The new ligands are readily prepared, as shown in Schemes 2 and 3. As shown below (Scheme 2) condensation of the trimethylaluminum complex of (R,R)-cyclohexanediamine with 2-fluoromethylbenzoate produced the fluoroimidazoline 4 in 85% yield. Fluoride displacement with commercially available $Ph_2PK$ in refluxing THF provided the phosphinoimidazoline 5 of Formula (1), where X, Y and Z are H, M is P, R1 is H and R2 and R3 form a fused cyclohexyl ring in 65% yield without chromatography.

Scheme 2

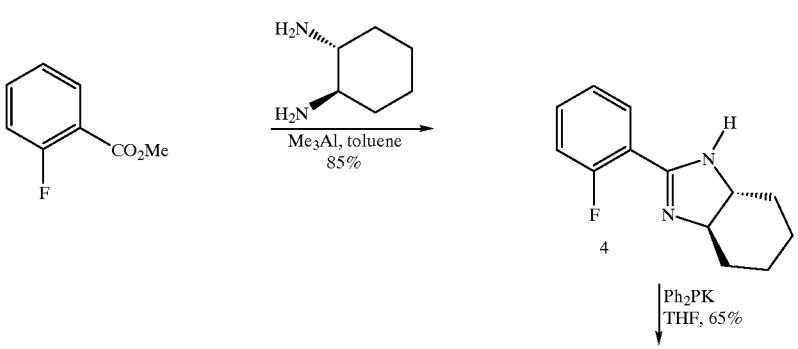

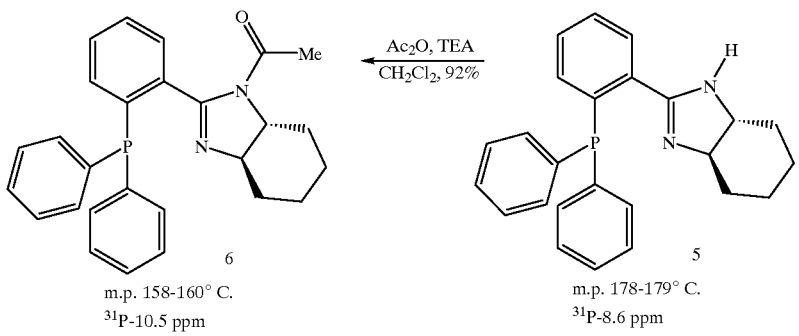

| 6 | 5 |
|---|---|
| m.p. 158-160° C. | m.p. 178-179° C. |
| $^{31}$P -10.5 ppm | $^{31}$P -8.6 ppm |

Acylation of 5 produced in high yield the phosphinoimidazoline 6 of Formula (1), where R1 is acetyl and X, Y, Z, M, R2 and R3 are as described for 5.

Alternatively, a typical ligand can be prepared as shown in Scheme 3, below. Formation of imidate 7 from 2-fluorobenzamide is accomplished with triethyloxonium tetrafluoroborate. Condensation of the imidate with a chiral diamine such as (S,S)-1, 2-diphenylethylenediamine then readily furnished fluoroimidazoline 8. Displacement of the fluoride with potassium diphenylphosphide, followed by acylation with 2-naphthoyl chloride then furnished ligand 10, of Formula (1), where R1 is 2-naphthoyl, X, Y, and Z are hydrogen, M is P, and R2 and R3 are both (S)-phenyl.

Other ligands of Formula (1) can be prepared by methods analogous to those described above.

EXPERIMENTAL SECTION

Synthesis of a typical ligand, 10 (See Scheme 3):

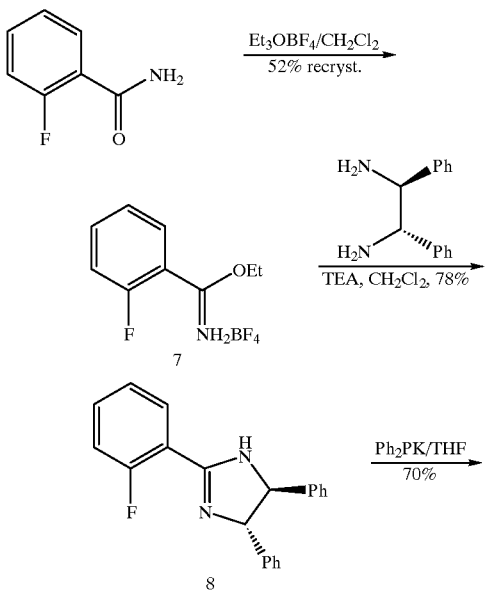

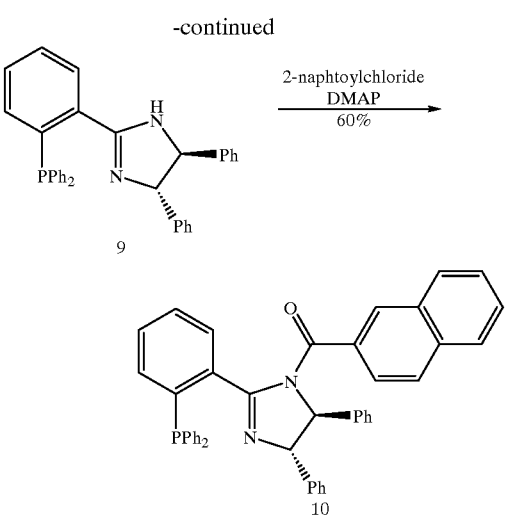

2-Fluoro-ethylbenzimidate tetrafluoroborate (7):

To 13.6 g 2-fluorobennamide (98 inmol, 1 eq.) was added 100ml 1M triethyloxonium terafluoroborate/methylene chloride solution (100 mmol, 1.02 eq.) via canula under N$_2$. After stirring 18 h at ambient temperature, the reaction mixture was filtered, and the resultant solid recrystallized from 100ml ethyl acetate to give 13.0 g of 2-fluoro-ethylbenzimidate tetrtuoroborate 7 (52% recrystallized) as a colorless solid. M.p. 128–131° C.; $^{19}$F NMR (DMSO)δ: –113.8, –154.2 ppm.

2-(2'-Fluorophenyl)-(4S,5S)-diphenyl-4,5-dihydroimidazole (8):

To a 100 ml flask was charged 5.00 g imidate 7 (19.6 mmol, 1 eq.), 4.16 g (S,S)-1, 2-diphenylethylenediamine (19.6 mmol, 1 eq.), 50 ml dichloromethane, and 6.3 ml triethylamine (45.3 mmol, 2.3 eq.) in the order given. After stirring 4 hours at ambient temperature, the reaction mixture was poured into 50 ml water, the phases separated, and the aq. phase reextracted with dichloromethane. The combined methylene chloride layers were washed with 2% aq. ammonium chloride, dried with magnesium sulfate, filtered, and the filtrate evaporated in vacuo to give an oil. This oil was dissolved in 25 ml boiling hexane, cooled to 0°, filtered and air dried to give 4.80 g of 2-(2'-fluorophenyl)-(4S,5S)-diphenyl4,5-dihydroimidazole 8 (78%) as a colorless solid. M.p. 122–124° C.; MS (ES+): MH+317; $^{19}$F NMR (CDCl$_3$) δ: –113.6 ppm.

2-(2'-Diphenylphosphinophenyl)-(4S,5S)-diphenyl-4,5-dihydroimidazole (9):

13.9 ml of 0.5M potassium diphenylphosphide/THF (6.95 mmol, 1.1 eq.) was heated to 60° in a thermostated oil bath.

To this warm solution was then added a solution of 2.00 g fluoride 8 (6.32 mmol, 1 eq.) in 5 ml THF via syringe over 2 minutes. The resulting solution was then heated at reflux for 1 hour, cooled to room temperature and quenched by the addition of 10 ml water. The resulting mixture was extracted with methylene chloride (2×25 ml), dried (MgSO$_4$), and the solvents removed in vacuo to give an oil.

This oil was then chromatographed on C18 silica gel eluting with 5:1 acetonitrile:water to give, after drying under high vacuum, 2.13 g (70%) of 2-(2'-diphenylphosphinophenyl)- (4S,5S)-diphenyl-4,5-dihydroimidazole 9 as a colorless, amorphous foam. MS (ES+): MH+483; $^{31}$P NMR (CDCl$_3$)δ: −9.6 ppm.

2-(2'-Diphenylphosphinophenyl)-3-(2"-naphthoyl)-(4S,5S)-diphenyl-4,5-dihydroimidazole (10):

A 10 ml round bottom flask was charged with 150 mg dihydroimidazole 9 (0.311 mmol, 1 eq.), 76 mg p-dimethylaminopyridine (0.622 mmol, 2 eq.), 1.5 ml of 1,2-dichloroethane, and 89 mg 2-naphthoyl chloride (0.467 mmol, 1.5 eq.) in the order given. After 1 hour, the volatiles were removed in vacuo and the residue chromatographed on silica gel eluting with 2% methanol/dichloromethane to give 117 mg of the ligand, 2-(2'-diphenylphosphinophenyl)-3-(2"-naphthoyl)-(4S,5S)-diphenyl-4,5-dihydroimidazole (10) (60%) as a colorless foam. MS (ES+): MH+637; $^{31}$P NMR (CDCl$_3$) δ: −11.0 ppm.

Typical use of the invention in asymmetric synthesis (See Scheme 4):

Scheme 4

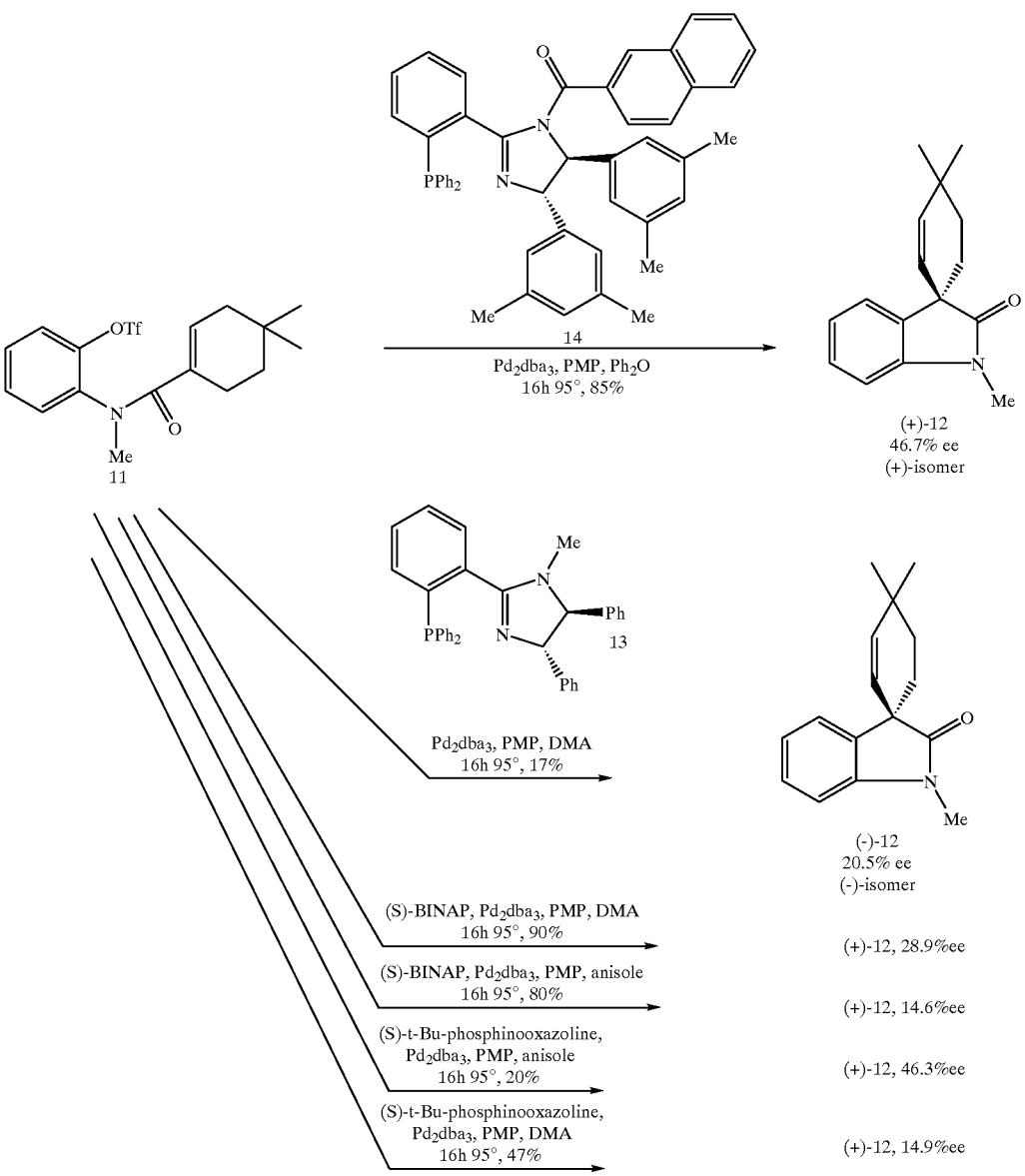

A 10 ml headspace vial was charged with 11.4 mg Pd$_2$dba$_3$ (0.0125 mmol, 0.05 eq.), 19.1 mg ligand 14 (0.0275 mmol, 0.11 eq.) and 1.5 ml Ph$_2$O. The resulting solution was evacuated/filled with Ar (3×), then placed in a preequilibrated 50° oil bath for 1 hour. To the resulting solution was then added a solution of triflate 11 (98mg, 0.25 mmol, 1 eq.), pentamethylpiperidine (MP, 181 microliters, 1.00 mmol, 4 eq.) and 1.0 ml Ph₂O via syringe, at once. The resulting solution was heated 16h at 95°, cooled, and chromatographed directly on silica gel eluting with 4:1 hexane:ethyl acetate to give 51 mg of spirolactam 12 (85% yield). Analysis of this material by chiral HPLC using a Chiracel OD column, 250 mm×4.6 mnm, using 99:1 Hexane:IPA at a flow rate of 1.0 ml/minute, revealed the enantiomeric excess of the product to be 46.7%, that is, 46.7%ee. The enantiomer obtained with this ligand, where R1 was an electron withdrawing group, was the (+)-isomer. When the reaction was repeated with ligand 13, where R1=methyl, an electron donating group, the opposite enantiomer, the (−)-isomer, was obtained, in 20.5%ee. Although this initial method is not yet fully optimized, the concept of controlling enantioselectivity by electronic tuning of the R1 substituent is clearly

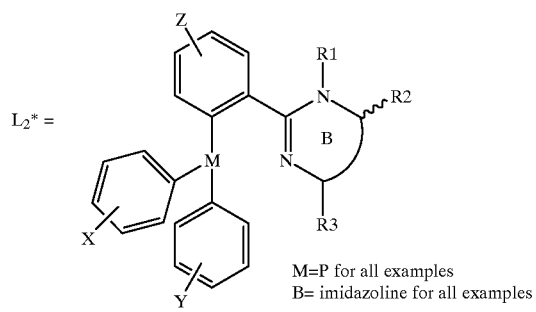

M=P for all examples
B= imidazoline for all examples

TABLE 1

Ligands Evaluated for the Asymmetric Heck Reaction.

| Entry | R1 | R2,R3 | X, Y, Z | Solvent | Yield | % ee | MI* |
|---|---|---|---|---|---|---|---|
| 1 | Acetyl | (S,S)-diphenyl | X = Y = Z = H | Anisole | 68% | 31.2 | 1, (+) |
| 2 | Benzoyl | (S,S)-diphenyl | X = Y = Z = H | Anisole | 60% | 36.0 | 1, (+) |
| 3 | Benzoyl | (S,S)-diphenyl | X = Y = Z = H | Ph₂O | 76% | 42.2 | 1, (+) |
| 4 | Benzoyl | (S,S)-diphenyl | X = Y = Z = H | p-Dioxane | 66% | 47.1 | 1, (+) |
| 5 | p-phenyl-benzoyl | (S,S)-diphenyl | X = Y = Z = H | Ph₂O | 73% | 40.5 | 1, (+) |
| 6 | Methyl | (S,S)-diphenyl | X = Y = Z = H | DMA | 17% | 20.5 | 2, (−) |
| 7 | p-methoxybenzoyl | (S,S)-diphenyl | X = Y = Z = H | Anisole | 60% | 33.4 | 1, (+) |
| 8 | p-methoxybenzoyl | (S,S)-diphenyl | X = Y = Z = H | Ph₂O | 27% | 47.6 | 1, (+) |
| 9 | p-cyanobenzoyl | (S,S)-diphenyl | X = Y = Z = H | Ph₂O | 83% | 36.6 | 1, (+) |
| 10 | 1-napthoyl | (S,S)-diphenyl | X = Y = Z = H | Ph₂O | 85% | 40.6 | 1, (+) |
| 11 | 2-napthoyl | (S,S)-diphenyl | X = Y = Z = H | Ph₂O | 68% | 44.6 | 1, (+) |
| 12 | t-butoxycarbonyl (BOC) | (S,S)-diphenyl | X = Y = Z = H | Ph₂O | 92% | 32.5 | 1, (+) |
| 13 | p-methoxybenzoyl | (S,S)-di-(m-xylyl) | X = Y = Z = H | Ph₂O | 88% | 41.8 | 1, (+) |
| 14 | 2-napthoyl | (S,S)-di-(m-xylyl) | X = Y = Z = H | Ph₂O | 85% | 46.7 | 1, (+) |
| 15 | p-methoxybenzoyl | (S,S)-diphenyl | X = Y = H; Z = benzo fused (napthalene) | Ph₂O | 8% | 35.3 | 1, (+) |
| 16 | p-methoxybenzoyl | (R,R)-di-(p-methoxyphenyl) | X = Y = Z = H | Ph₂O | 20% | 33.4 | 2, (−) |
| 17 | p-dimethylamino benzoyl | (R,R)-diphenyl | X = Y = Z = H | Ph₂O | 25% | 37.0 | 2, (−) |
| 18 | Acetyl | (R,R)-cyclohexyl | X = Y = Z = H | Anisole | 10% | 29.2 | 1, (+) |

*MT = Major Isomer: 1 = first eluted, (+)-isomer; 2 = second eluted, (−)-isomer.
Notes: 1) All reactions at 100° C. unless otherwise noted.
2) All ee's determined by chiral HPLC (see "Typical use of the invention in asymmetric synthesis" (Scheme 4) section).
3) M = P for all ligands.
4) B ring = imidazoline (5 membered ring) for all ligands
5) X = Y = H for all ligands
6) Z = H for all ligands except entry 15 where Z = fused benzo ring (naphthalene) 7) All yields are for isolated, chromatographically pure 12.

validated. When commercial (S)-BINAP was examined for this transformation, the product obtained, (+)-12, using Ph₂O as solvent, was formed in 90% yield, yet only 14.6% ee, while in dimethylacetamide as solvent, the yield was 80%, and the observed enantiomeric excess was only 28.9% ee. When the (S)-t-butyl phosphinooxazoline of Pfaltz/Helmchen/Williams was used in anisole, the isolated yield of (+)-12 was only 20%, and the observed enantiomeric excess was 46.3%ee. When that ligand was used in dimethylacetamide, the isolated yield was higher, 47%, yet the enantiomeric excess was only 14.9% ee. Table 1, shows results for 18 of the new ligands when evaluated in the asymmetric Heck reaction.

While in the foregoing description the detailed embodiments of the present invention have been set forth, it will be understood by those skilled in the art that considerable variation may be made in such detail without departing from the spirit of the invention.

What is claimed is:

1. A compound of Formula (1)

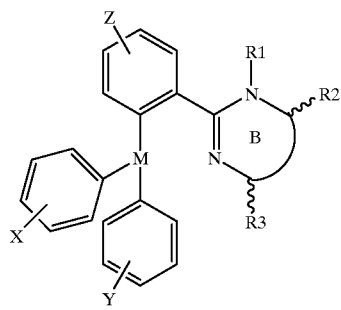

M is Phosphorous;

R1 is hydrogen; $C_1$–$C_{10}$ alkyl; branched alkyl or cycloalkyl; aryl selected from the group consisting of phenyl and naphthyls; substituted aryl wherein the aryl is as hereinbefore defined and the substituents, which may be one or more, or are selected from the group consisting of alkyl, halogen, alkoxy, acyl, phenoxy, cyano, nitro, hydroxy, amino, alkylamino, dialkylamino, carboalkoxy, amido and sulfoxy, heteroaryl selected from the group 2-pyridyl, 3-pyridyl, 4-pyridyl, 2-furyl, 3-furyl, 2-benzofuryl, 3 benzofuryl, 2-thiophenyl, 3-thiophenyl, 2-benzothiophenyl, 3-benzothiophenyl, 2-pyrrolyl, 3-pyrrolyl, 2-indolyl, 3-indolyl, benzimidazolyl, imidazolyl, quinolinyl, isoquinolinyl, oxazolyl, benzoxazolyl, thiazolyl, and pyrimidinolyl, which may be optionally substituted with one or more alkyl, halogen, alkoxy, acyl, phenoxy, cyano, nitro, hydroxy, amino, alkylamino, dialkylamino, carboalkoxy, amido, or sulfoxy group; $C_{2-6}$ acyl; aroyl selected from the group benzoyl and napthoyl, which may be optionally substituted with one or more substituents as set forth above for aryl; heteroaroyl selected from the group 2-furoyl, 3-furoyl, 2-pyridoyl, 3-pyridoyl, 4-pyridoyl, 2-benzofuranoyl, 3-benzofuranoyl, 2-thiophenoyl, 3-thiophenoyl, 2-benzothiophenoyl, 3-benzothiophenoyl, 2-pyrroyl, 3-pyrroyl, 2-indoloyl, 3-indoloyl, benzimidazoyl, imidazoyl, quinolinoyl, isoquinolinoyl, oxazoyl, benzoxazoyl, thiazoyl, and pyrimidoyl, which may be optionally substituted with one or more substituents as set forth above for heteroaryl; $SO_2R4$ where R4 is selected from the group alkyl, aryl and heteroaryl, which aryl and heteroaryl may be optionally substituted as described above;

R2 and R3 can be the same or different and are hydrogen, aryl or heteroaryl as defined above, substituted aryl or heteroaryl as defined (with substituents as defined above), alkyl, branched alkyl, cycloalkyl, benzyl, substituted benzyl, with substituents as defined for aryl, or R2 and R3 together may form a fused carbocyclic ring;

X, Y and Z can be independently selected from hydrogen, aryl (pendant or fused) as hereinbefore defined, halogen, $C_1$–$C_{10}$, alkoxy cyano, nitro, amino, alkylamino, dialkylamino, —$CO_2H$, —CO(lower alkoxy), —CO(lower alkyl), —NCOH, —NCO (lower alkyl), $NSO_2$(alkyl), —$NSO_2$(aryl), hydroxy, alkyl, sulfonoxyalkyl, sulfonoxyaryl, or alkoxyalkyl;

Ring B is an imidazoline ring or a tetrahydropyrimidine ring;

and at least one, or both, of R2 and R3 must be attached to a chiral carbon, of either (R) or (S) absolute configuration.

2. An improved method for synthesizing asymmetric compounds wherein specific enantiomers are obtained by use of catalysts palladium, nickel, rhodium, platinum, ruthenium, cobalt, iridium or copper, wherein the improvement comprises use of a compound as recited in claim 1.

* * * * *